United States Patent [19]
Mulier et al.

[11] Patent Number: 6,096,037
[45] Date of Patent: Aug. 1, 2000

[54] TISSUE SEALING ELECTROSURGERY DEVICE AND METHODS OF SEALING TISSUE

[75] Inventors: Peter M. J. Mulier, Stillwater; Michael F. Hoey, Shoreview, both of Minn.

[73] Assignee: Medtronic, Inc., Minneapolis, Minn.

[21] Appl. No.: 08/901,890

[22] Filed: Jul. 29, 1997

[51] Int. Cl.⁷ .................................................... A61B 18/18
[52] U.S. Cl. ............................... 606/49; 606/51; 607/101
[58] Field of Search .................................. 606/40, 42, 41, 606/46, 49, 50–52, 205; 607/101, 98, 102

[56] References Cited

U.S. PATENT DOCUMENTS

| | | | |
|---|---|---|---|
| 5,167,659 | 12/1992 | Ohtomo et al. | 606/40 |
| 5,217,460 | 6/1993 | Knoepfler | 606/52 |
| 5,300,087 | 4/1994 | Buysse et al. | |
| 5,318,589 | 6/1994 | Lichtman | |
| 5,364,394 | 11/1994 | Mehl | |
| 5,395,312 | 3/1995 | Desai | |
| 5,403,312 | 4/1995 | Yates et al. | |
| 5,431,649 | 7/1995 | Mulier et al. | |
| 5,458,598 | 10/1995 | Feinberg et al. | |
| 5,584,872 | 12/1996 | LaFontaine et al. | 607/116 |
| 5,609,151 | 3/1997 | Mulier et al. | |
| 5,964,755 | 10/1999 | Edwards | 606/41 |

FOREIGN PATENT DOCUMENTS

WO 95/31144 11/1995 WIPO.
WO 97/05829 2/1997 WIPO.

*Primary Examiner*—Linda C. M. Dvorak
*Assistant Examiner*—Roy Gibson
*Attorney, Agent, or Firm*—Harold R. Patton; Michael J. Jaro

[57] ABSTRACT

An electrosurgery medical device is enhanced with unique solution-assistance, and includes, in combination, co-operating device jaws including jaw portions for manipulating tissue, and a plurality of solution infusion openings defined and spaced along each of the jaw portions, for receiving electrolytic solution and infusing the solution onto and into tissue to be manipulated, along said jaw portions. As preferred, the device further comprises at least one, and most preferably, many, longitudinal groove(s) along at least one and most preferably, both, of the jaw portions, with the solution infusion openings located in the groove or grooves. The solution is energized with RF energy and contributes to the functions and beneficial effects of the instrument. The solution exits the openings in the grooves at sufficient flow rates to separate substantially all the operative surfaces of the device from tissue, thereby substantially completely preventing adherence between the operative surfaces and tissue. The solution is further energized to a range of energy densities such that tissues to be affected are sealed against flow of blood, lymphatic fluids, air, and other bodily fluids and gases.

20 Claims, 9 Drawing Sheets

TISSUE SEALING ELECTROSURGERY DEVICE AND METHODS OF SEALING TISSUE

BACKGROUND OF THE INVENTION

This invention relates to medical instruments, and more particularly to electrosurgical devices, and methods of manipulating tissue as, for example, by cutting the tissue.

DESCRIPTION OF THE RELATED ART

High-frequency alternating current was used to cut and coagulate human tissue as early as 1911. Current generators and electrode tipped instruments then progressed such that electrosurgical instruments and current generators are available in a multitude of configurations for both open procedures and endoscopic procedures, with microprocessor-controlled currents typically on the order of 500 KHz. Radiofrequency (RF) catheter ablation of brain lesions began in the 1960s, and RF ablation of heart tissue to control supraventricular tachyarrhythrnias began in the 1980s. Thus, electrical energy, including but not limited to RF energy, is a known tool for a variety of effects on human tissue, including cutting, coagulating, and ablative necrosis, with and as a part of electrically conductive forceps. Bipolar and monopolar currents are both used with electrosurgical forceps. With monopolar current, a grounding pad is placed under the patient. A recent example of an electrically energized electrosurgical device is disclosed in U.S. Pat. No. 5,403,312 issued on Apr. 4, 1995 to Yates et al., and the disclosure is incorporated by reference.

SUMMARY OF THE INVENTION

An object of the present invention is to provide an electrosurgery tissue sealing medical device which may and also may not be a forceps.

Another object of the present invention is to provide an electrosurgery tissue sealing device such as a forceps that seals tissue by a unique flow of an electrolytic fluid or solution to the manipulating portions of the device in combination with energization of the solution with electrical energy. The effect of the solution and energy may be enhanced with pressure. The solution is brought into contact with and infuses the tissue. The solution may include saline as well as other non-toxic and toxic electrolytic solutions, and may be energized with RF electrical energy. The body of the device itself may or not be energized.

The solution provides at least in part the beneficial functions and effects of the instrument. As preferred, pressure on the tissue is applied, and most preferably the effect of pressure is optimized, as by applying pressure across the tissue to be effected that is substantially uniform.

Another object of the invention is to provide an electrosurgery medical device as described, and methods of sealing tissue, in which tissues are sealed against flow of fluids including air. With the invention, for example, lung tissue is aerostatically and hemostatically sealed, with the tissue adjacent the sealed tissue retaining blood and air.

Another object of the invention is to provide an electrosurgery medical device that may take the form of open surgery forceps of a variety of specific forms, or endoscopic forceps, also of a variety of forms.

A further object of the invention is to provide an electrosurgery medical device as described, in which the electrolytic solution by which the instrument functions is infused from the device onto and/or into the tissue along the operative portions of the device. With and without applied pressure, the solution coagulates and additionally seals tissue, as a result of being energized by RF energy, and also envelopes the operative portions of the device in solution all during manipulation of tissue, substantially completely preventing adherence between the instrument and tissue, substantially without flushing action.

In a principal aspect, then, the invention takes the form of an enhanced solution-assisted electrosurgery medical device comprising, in combination, co-operating device jaws including jaw portions for manipulating tissue, and a plurality of solution infusion openings defined and spaced along each of the jaw portions, for receiving solution and infusing solution onto and into the tissue along said jaw portions. While the device is contemplated with and without grooves, as preferred, the device further comprises at least one, and most preferably, many, longitudinal grooves along at least one and most preferably, both, of the jaw portions. Also most preferably, the solution infusion openings are located on the inside faces of the jaw portions, adjacent to and most preferably in the groove or grooves. The solution exiting the openings separates substantially all the operative surfaces of the device from tissue, substantially completely preventing adherence between the operative surfaces and tissue. The solution also aids in coagulation.

Coagulation aside, the invention causes hemostasis, aerostasis, and more generally, "omnistasis" of substantially any and all liquids and gases found in tissue being treated, such as lymphatic fluids and methane, as well as blood and air. These broader effects are understood to result from such actions as shrinkage of vasculature with and without coagulation, and without desiccation and carbonization.

Also as preferred, the operative portions of the device may take the form of a circular, semicircular or other regular and irregular geometric shape, to contain and/or isolate tissue to be affected and perhaps resected. As an example, with an enclosed geometric shape such as a circle, tissue surrounding lesions and/or tumors of the lung may be aerostatically and hemostatically sealed, resulting in an isolation of the lesions and/or tumors for resection. Lung function is retained. For adaption to unique tissue geometries, the operative portions of the device may be malleable, to be manipulated to substantially any needed contour. For procedures including resection, the device may include an advanceable and retractable blade, or additional functional structures and features.

These and other objects, advantages and features of the invention will become more apparent upon a reading of the detailed description of preferred embodiments of the invention, which follows, and reference to the drawing which accompanies this description.

BRIEF DESCRIPTION OF THE DRAWING

The accompanying drawing includes a variety of figures. Like numbers refer to like parts throughout the drawing. In the drawing.

DESCRIPTION OF THE PREFERRED EMBODIMENTS

Figure 1:
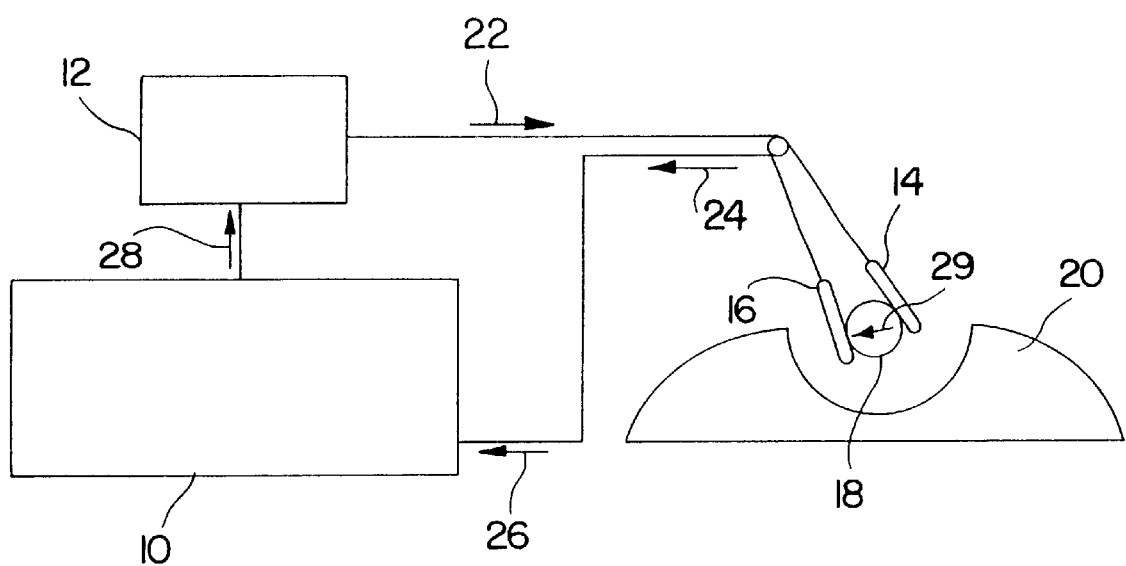
FIG. 1 is a schematic diagram of the key elements of an electrical circuit according to the invention.

Electrosurgery uses electrical energy to heat tissue and cause a variety of effects such as cutting, coagulation and ablative necrosis. The heat arises as the energy dissipates in the resistance of the tissue. The effect is dependent on both temperature and time. Lower temperatures for longer times often yield the same effect as higher temperatures for shorter times. Normal body temperature is approximately 37° C. No significant long-term effect is caused by temperatures in the range of 37° C. to 40° C. In the range of 41° C. to 44° C., cell damage is reversible for exposure times less than several hours. In the range of 45° C. to 49° C., cell damage becomes irreversible at increasingly short intervals. The following table states expected effects at higher temperatures:

| Temperature (° C.) | Effect |
| --- | --- |
| 50–69 | Irreversible cell damage - ablation necrosis. |
| 70 | Threshold temperature for shrinkage of tissue. (Some collagen hydrogen bonds break at 60–68; those with cross-linkages break at 75–80.) |
| 70–99 | Range of coagulation. Hemostasis due to shrinkage of blood vessels. |
| 100 | Water boils. |
| 100–200 | Desiccation as fluid is vaporized. Dependent on the length of time during which heat is applied, carbonization may occur, and at higher temperatures, occurs quickly. |

This table is not intended as a statement of scientifically precise ranges above and below which no similar effects will be found, and instead, is intended as a statement of generally accepted values which provide approximations of the ranges of the stated effects. Limitation of the appended claims in accordance with this and the further details of this description is intended to the extent such details are incorporated in the claims, and not otherwise.

As a consequence of the foregoing effects, preferred "soft" coagulation occurs at temperatures slightly above 70° C. Heat denatures and shrinks tissues and blood vessels, thereby leading, as desired, to control of bleeding. Cells are generally not ruptured. "Soft" coagulation is generally assured with voltages below 200 peak Volts. Sparks are avoided. "Forced" coagulation can be accomplished with bursts of electrical energy. Electric arcs are generated. Deeper coagulation is achieved, at the cost of some carbonization and an occasional cutting effect. Spray coagulation is also possible. Tissue cutting occurs by desiccation, when the concentration of electrical energy, also referred to here as energy density, is acute, and the temperature of tissue is raised above 100° C.

For both coagulation and cutting by electrical energy, a sine wave waveform is employed, with a frequency of about 500 kHz. For cutting, increasing voltage to as much as 600 peak Volts leads to higher spark intensity which results in deeper cuts. Frequencies above 300,000 Hz avoid stimulating nerve and muscle cells, and generally assure that the effect on tissue is substantially purely thermal.

In contrast with the RF energy tissue-cutting electrosurgery tools of the past, significant purposes of the present invention are to provide a mechanism of avoiding desiccation of tissue at the electrode/tissue interface and to achieve sealing of tissues. By "sealing," the effects of hemostasis, or arresting of bleeding; "aerostasis," or arresting of the passage of air; and closure of tissues such as blood vessels against larger-scale passage of blood, among other effects, are intended. More specifically, the effect of sealing at the cellular level is a primary focus, as is sealing at the vascular level.

Referring to FIG. 1, key elements of a preferred electrical circuit according to the invention include an electrosurgical unit 10, a switch 12, and electrodes 14, 16. An effect is created on tissue 18 of a body 20. One electrode such as electrode 14 acts as a positive or active electrode, while the other such as electrode 16 acts as a negative or return electrode. Current flows directly from one electrode to the other primarily through only the tissue, as shown by arrows 22, 24, 26, 28, 29. No pad is needed under the patient. This is a bipolar configuration.

Figure 2:
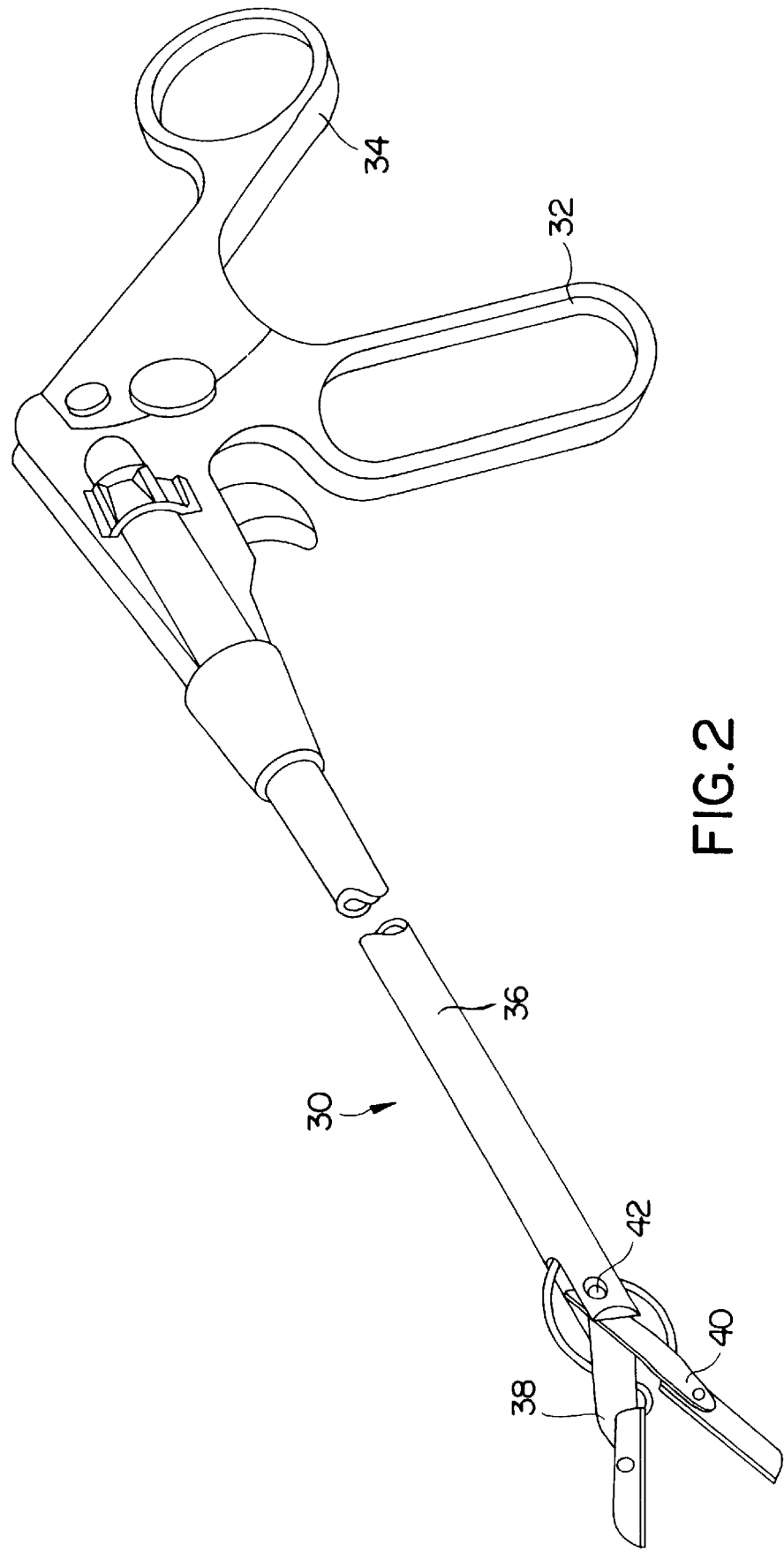
FIG. 2 is a perspective view of an endoscopic forceps according to the invention.
Figure 3:
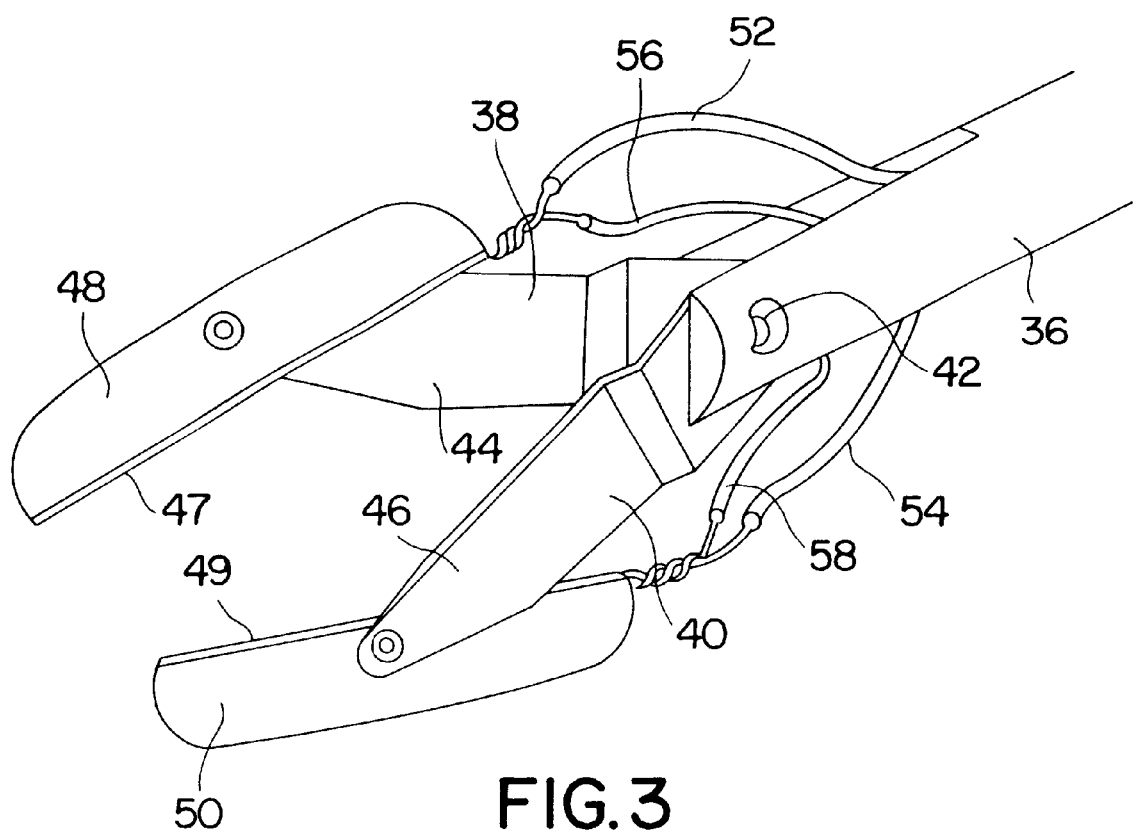
FIG. 3 is a detail view of a portion of the forceps of FIG. 2.

Referring to FIG. 2, a forceps 30 according to the invention is an endoscopic forceps, and includes manual handles 32, 34, an elongated shaft 36, and jaws 38, 40. The handles 32, 34 pivot together and apart and through a suitable mechanism (not shown; present in the incorporated prior art) control the jaws 38, 40 to also pivot together and apart about a pivot connection 42. Referring to FIG. 3, each jaw 38, 40 is formed in two parts, hinged together. The jaw 38 includes a link portion 44 connected directly to the forceps shaft 36, and the jaw 40 includes a link portion 46 also connected directly to the forceps shaft 36. A jaw portion 48 hingedly fastened to the jaw link portion 44 completes the jaw 38; a jaw portion 50 hingedly fastened to the jaw link portion 46 completes the jaw 40.

As stated in the background of the invention, a wide variety of alternatives to the structure described and shown in FIG. 2 are possible. Prominent examples from those incorporated include the structures of U.S. Pat. No. 5,403,312 (Yates et al.) issued Apr. 4, 1995; U.S. Pat. No. 5,395,312 (Desai) issued Mar. 7, 1995; and U.S. Pat. No. 5,318,589 (Lichtman et al.) issued Jun. 7, 1994.

Still referring to FIG. 3, a solution supply tube 52 supplies electrolytic solution to an electrode strip 47 along the jaw portion 48, as will be described. A solution supply tube 54 supplies electrolytic solution to a similar strip 49 along the jaw portion 50. A wire 56 electrically connects to the solution supply tube 52; a wire 58 electrically connects to the solution supply tube 54. All the supplies 52, 54, 56, 58, both solution and electrical, extend from the proximal or manual handle end of the shaft 36, and connect to solution and electrical sources.

Figure 4:
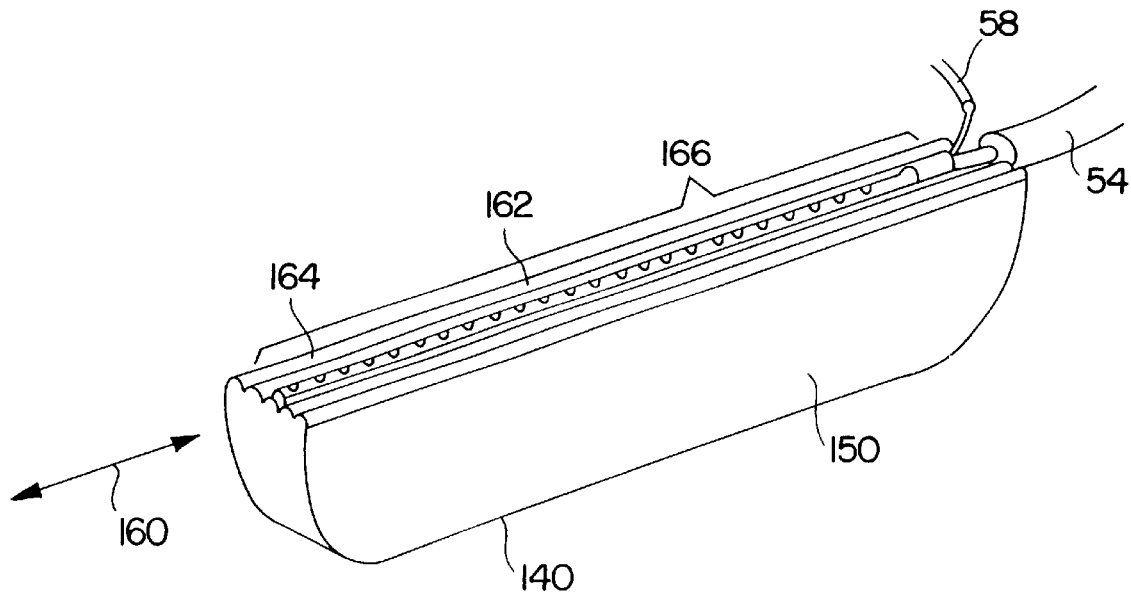
FIG. 4 is a perspective view of a modification of the embodiment of FIG. 2.

Referring to FIG. 4, and in a second form of a jaw, designated 140, a jaw portion 150 similar to jaw portion 50 in FIG. 3, includes a longitudinal dimension in the direction of arrow 160. A plurality of longitudinal grooves 162 are spaced side-by-side across the inner face 164 of the jaw portion 150. The grooves 162 extend the full longitudinal length of the jaw portion 150. The same is true of a mirror image jaw portion, not shown. Both jaw portions are incorporated in a structure as in FIG. 3, and could be placed in substitution for jaw portions 48, 50 in FIG. 3. Grooves, not shown, also preferably extend along the corresponding jaw portions 48, 50 of FIGS. 2–3. Orientations of the grooves other than longitudinal are considered possible, within the limit of construction and arrangement to substantially retain solution along the operative jaw portions.

Bodily tissues to be manipulated have a natural surface roughness. This roughness significantly reduces the area of contact between the forceps jaws and manipulated tissues. Air gaps are created between conventional smooth-surfaced jaws and tissues. If the jaws were energized when dry, electrical resistance in the tissues would be increased, and the current density and tissue temperature would be extremely high. In practice, tissue surfaces are sometimes wet in spots, and yet tissue wetness is not controlled, such that electrical power is to be set on the assumption the inner jaw surfaces are dry. This assumption is necessary to minimize unwanted arcing, charring and smoke.

In contrast, in a forceps according to the invention, whether the jaw portions are grooved or smooth, whether the grooves are longitudinal or otherwise oriented, the jaw portions are uniquely formed of a material such as hollow stainless steel needle tubing such that solution infusion openings 166 may be and are formed in the jaw inner faces such as the inner face 164, as in FIG. 4. Further, the solution supplies 52, 54 shown by example in FIG. 3 may and do open into the openings 166, to supply solution to the openings 166. As most preferred, the openings 166 are laser drilled, and have a diameter in a range centered around four thousandths (0.004) of an inch, and most preferably in a range from two to six thousandths (0.002–0.006) inches.

The purpose of the openings 166 is to infuse solution onto and/or into the tissue adjacent to and otherwise in contact with the forceps jaw portions inner surfaces. It is understood the openings are appropriately as small in diameter as described above to assure more even flow among the openings than would otherwise occur. Further, the openings need not be so closely spaced as to mimic the surface roughness as tissues. Microporous surfaces are possibly acceptable, while they are also not necessary. Infusion of fluid through the jaws is to be maintained in a continuous flow during and throughout the application of RF energy in order for the desired tissue effect to be achieved.

With the described structure and similar structures and methods within the scope of the invention, numerous advantages are obtained. Deeper and quicker coagulation is possible. The conductive solution infused onto and into the tissues maintains relatively consistent maximal electrical contact areas, substantially preventing hot spots and allowing higher power than soft coagulation. Little to no arcing, cutting smoke or char is formed. Jaw and tissue surface temperatures are lower than otherwise, resulting in significantly less adhesion of tissue to jaw surfaces, and substantially no desiccation. One mode of coagulation may be used in the place of the three modes soft, forced, and spray. Coagulation is possible of even the most challenging oozing tissues such as lung, liver and spleen tissues. Coagulation is more precise, where other coagulation modes sometimes spark to the sides and produce coagulation where not desired. Also, and importantly, electrosurgical cutting by desiccation may be avoided, and tissue sealing achieved. As desired, tissue sealing may occur alone, or be accompanied with mechanical cutting, as by a retractable and advancable blade as in U.S. Pat. No. 5,458,598, and as with blade 1210 in FIG. 12, or otherwise. The tissue sealing itself is understood to occur by flow of electrolytic solution to the manipulating portions of the forceps in combination with energization of the solution with electrical energy, and when included, in combination with pressure on, or compression of; the tissue. Compression of tissue is understood to deform tissues into conditions of sealing of tissues and especially vasculature. Compression of tissue followed by application of solution and energy is understood to permanently maintain compressed deformation of tissue, when present, and to shrink tissue and cause proteins to fix in place. Additional understanding of others is provided in the Yates et al. patent referenced above.

The body of the forceps itself may or not be energized. As most preferred, the solution primarily provides the beneficial functions and effects of the instrument. The effectiveness and extent of the tissue sealing is a function primarily of the type of tissue being manipulated, the quantity of electrolytic solution supplied to the tissue, and the power of the electrical energy supplied to the solution. Tissues not previously considered to be suitable for manipulation, as by cutting, are rendered suitable for manipulation by being sealed against flow of fluids, including bodily fluids and air. With the invention, for example, lung tissue may be cut after sealing, with the tissue adjacent the sealed tissue retaining blood and air. Examples of the principal parameters of specific uses of the invention are provided in the following table. It is understood that the combined consequences of the parameters are that energy density in the tissue to be treated is in a range to effect sealing of the tissue. However, in general, a power output of 7 to 150 watts is preferred.

| Fluid Quantity | Power | Tissue | Effect |
| --- | --- | --- | --- |
| 2 cc's per minute per electrode | 20 watts for 30 seconds | 1 cm diameter vessel | hemostasis through the vessel |
| 2 cc's per minute per electrode | 30 watts for 45 seconds | lung tissue | hemostasis and aerostasis |
| 4 cc's per minute per electrode | 40 watts for 90 seconds | 2 cm thickness liver tissue | hemostasis |

In the examples for which the table is provided, the electrolytic solution is saline. In the first example, the device in use was a device as in FIG. 2, with electrodes of 16 gauge tubing, 1 cm long. The tool in use in the second and third examples was a forceps as in FIG. 6, with jaw portions 348, 350, to be described, 4 mm wide and 2.8 cm long. No desiccation was observed at the tissue/electrode interface. The device of FIG. 2 is preferred for vessel closure.

A wide variety of the currently installed electrosurgical generators could and will provide proper waveforms and power levels for driving the described forceps. The waveforms need only be sine waves at about 500 kHz, and the power need only be about 30 or more watts. As example of available generators, Valleylab generators are acceptable and widely available.

Figure 8:
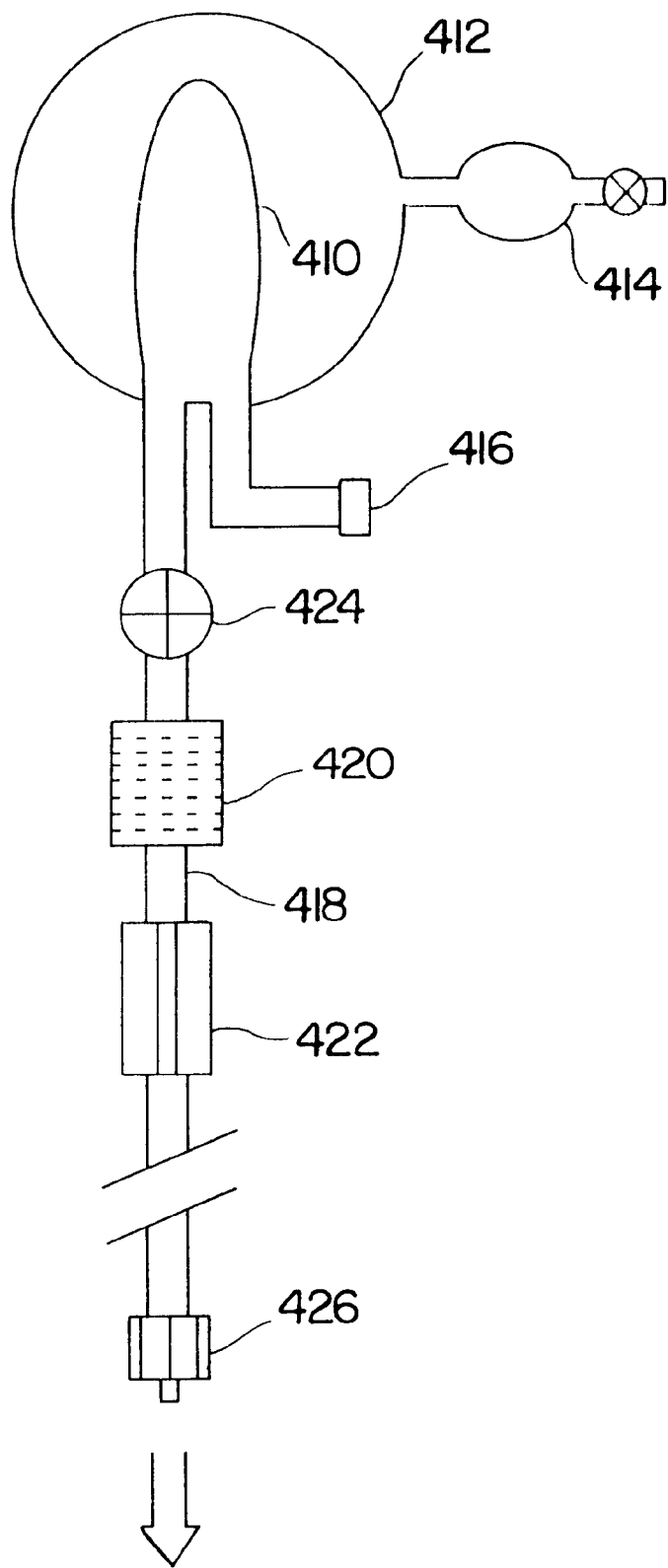
FIG. 8 is a schematic view of preferred saline supply equipment for the invention.

The electrolytic solution supplied to the forceps need only be saline, although a variety of non-toxic and toxic electrolytic solutions are possible. Toxic fluids may be desirable when excising undesired tissues, to prevent seeding during excision. Use of a pressure bulb is possible, as shown in FIG. 8. A flexible reservoir such as an intravenous (IV) bag 410 is surrounded with a more rigid rubber bulb 412 that is pressurized with air through an attached squeeze bulb 414. The reservoir is filled with solution through an injection port 416. An outflow line 418 has a filter 420 and a capillary tube flow restrictor 422 to meter flow. A clamp or valve 424 and connector 426 are also provided. A typical flow rate is one to two (1–2) cc/min at a maximum pressure of approximately sixteen pounds per square inch (16 psi)(52 mm Hg). An example of opening diameters, numbers, and flow rate is as follows: opening diameter, 0.16 mm; number of openings, 13 per cm; and flow rate, 2 cc's per minute. A long slit has also been used and found acceptable. In this embodiment, flow rates of 0.01 to 50 cc/min are preferred.

It is understood that highly significant to the invention is the spacing of a plurality of solution openings along the jaw inner surfaces. Single openings as in Ohta et al., that effectively pour fluid adjacent one portion of forceps, are generally not considered suitable or effective. Openings along outer surfaces of the jaws, opposite inner surfaces, are also generally not considered suitable or effective.

Figure 5:
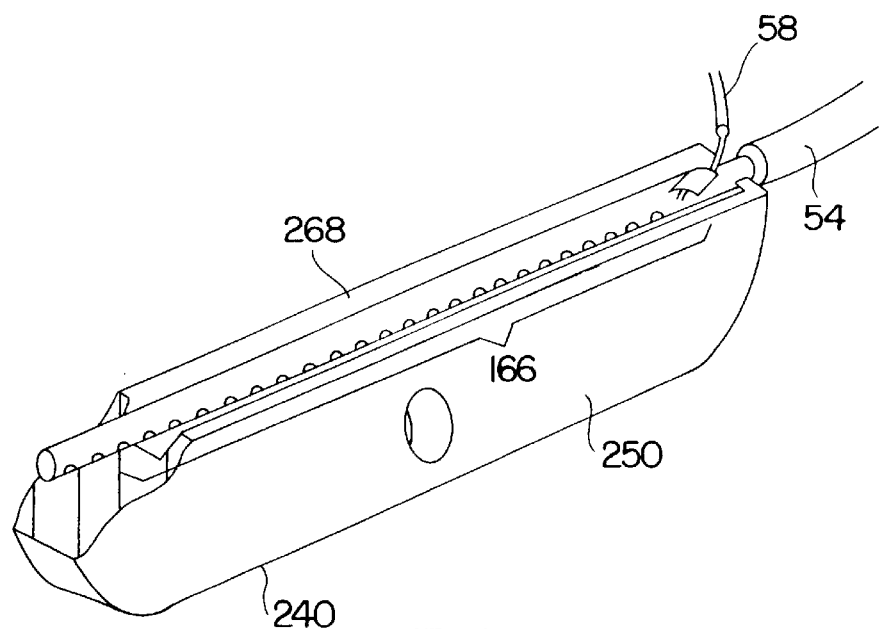
FIG. 5 is a second modification, of the embodiment of FIG. 4, shown partially broken away.

Referring to FIGS. 4 and 5, the configurations of the most preferred solution openings are disclosed. Referring to FIG. 5, in a jaw 240, longitudinally spaced openings 166 are rotated from those shown in FIG. 4, in a jaw portion 250, to turn the openings away from most direct contact with tissues, and more carefully eliminate any unintended plugging of the openings. Electrical insulators 268 in the form of elongated strips extend alongside the tubes which include the openings 166.

Figure 6:
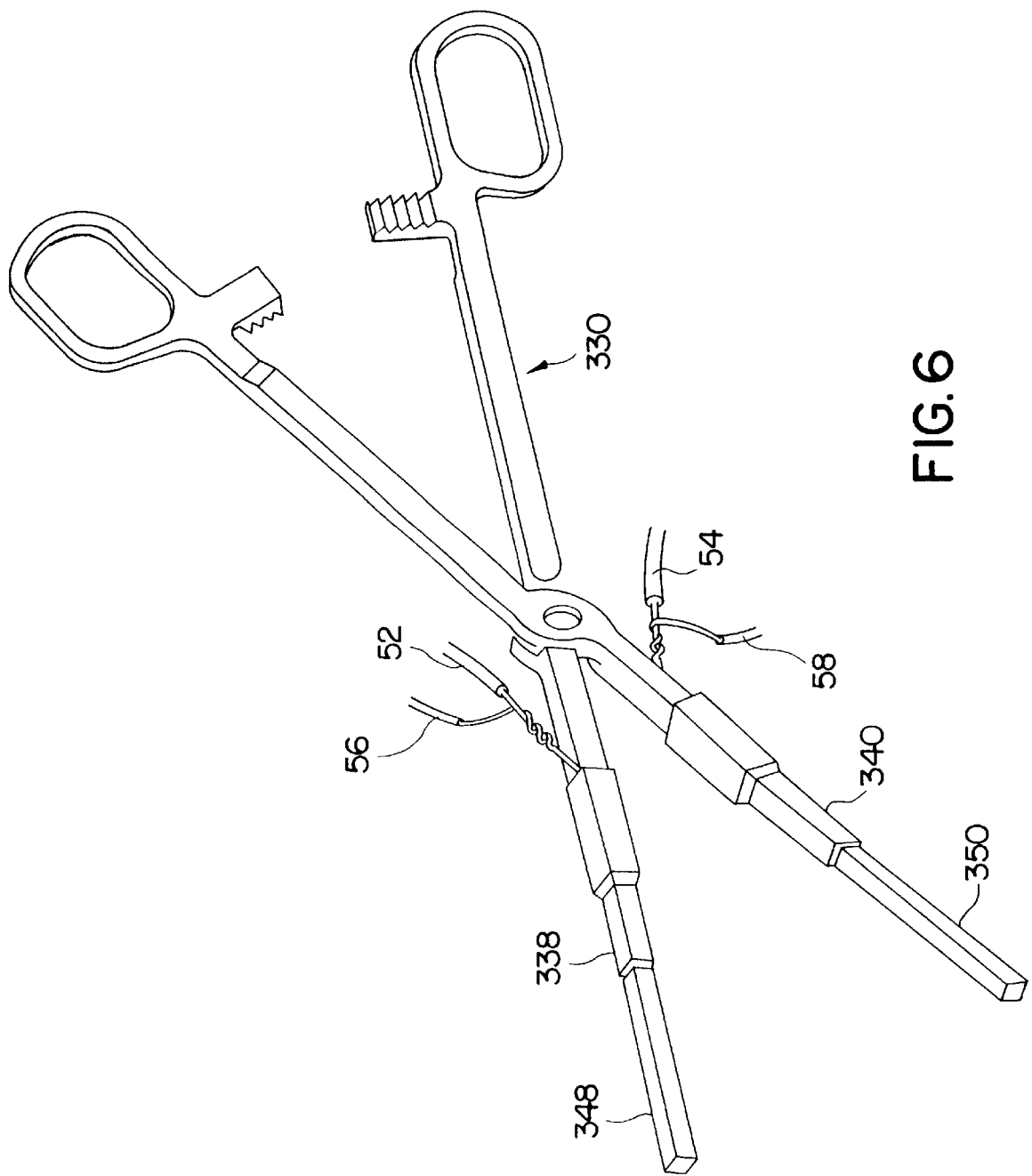
FIG. 6 is a perspective view of an open surgery forceps according to the invention.
Figure 7:
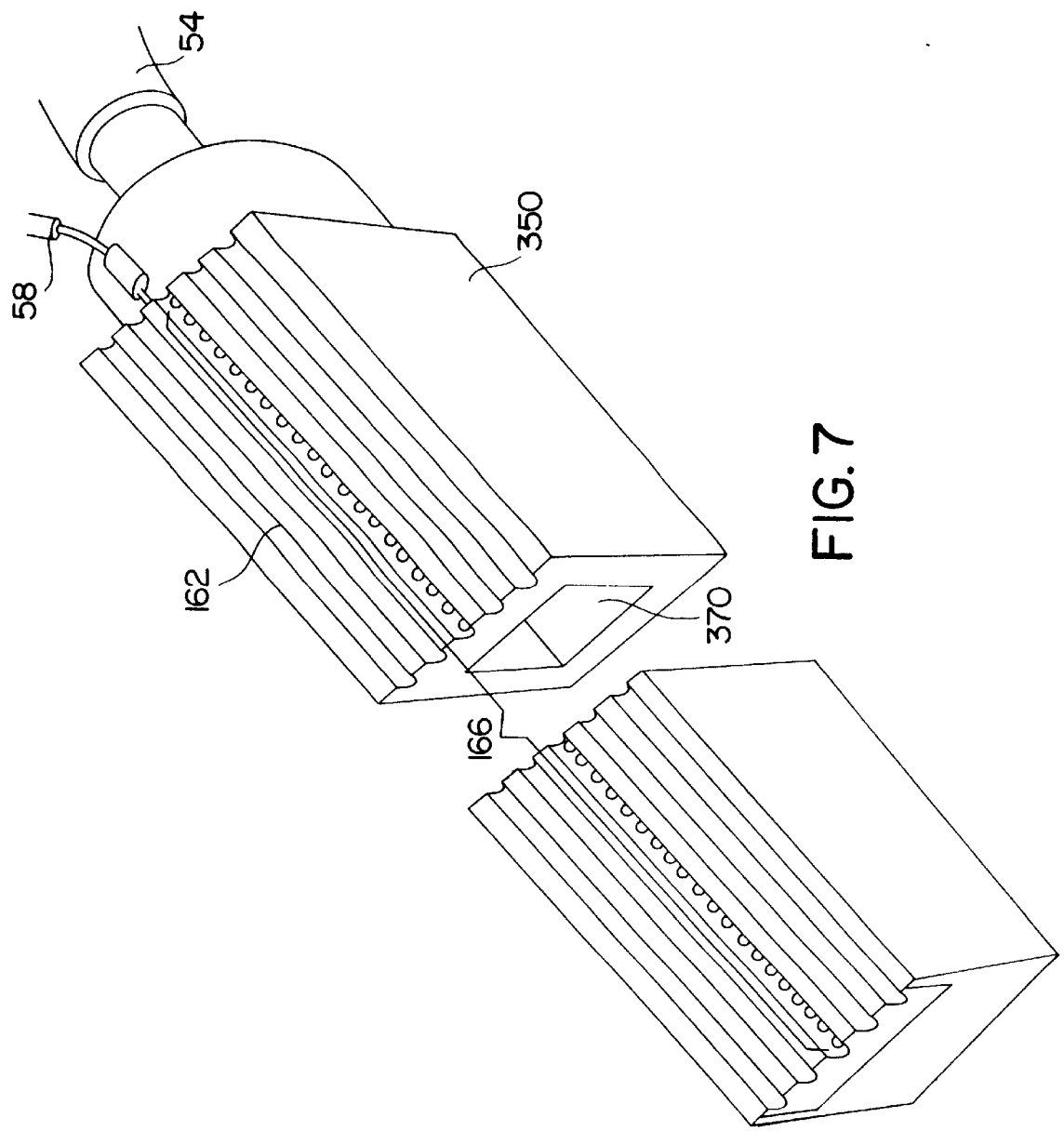
FIG. 7 is a detail view of a portion of the forceps of FIG. 6, partially broken away.

Referring to FIG. 6, open surgical forceps 330 include jaws 338, 340 with jaw portions 348, 350. As with jaw portion 350 in FIG. 7, the jaw portions 348, 350 include spaced solution infusion openings 166 in the central longitudinal groove of a plurality of grooves 162. A central channel 370 of both jaw portions 348, 350, as shown relative to jaw portion 350 in FIG. 7, supplies solution to the openings 166 from solution supplies 52, 54. As with the endoscopic forceps of FIGS. 2–5, the open surgical forceps 330 benefits from the unique enhancement of electrosurgical functions through the infusion of electrolytic solutions onto and into tissues through the spaced, laser drilled, solution infusion openings in the grooves 162.

Figure 9:
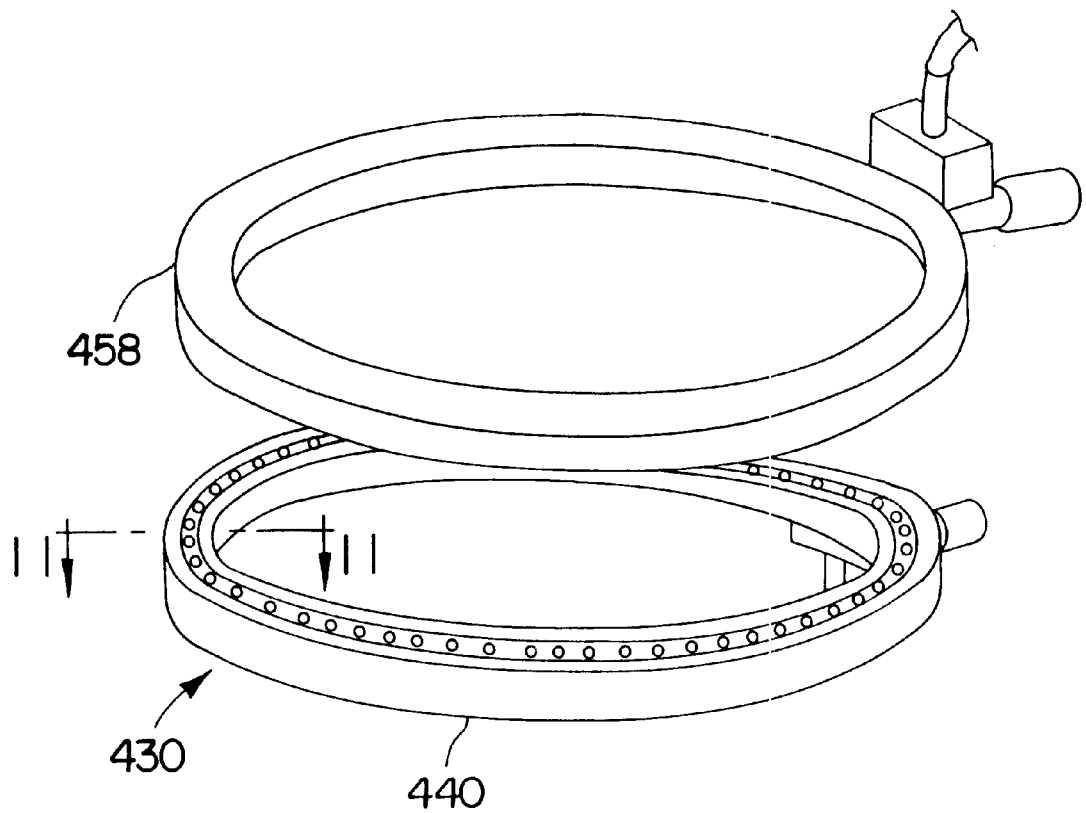
FIG. 9 is a perspective view of a portion of the jaws of an alternative device.
Figure 10:
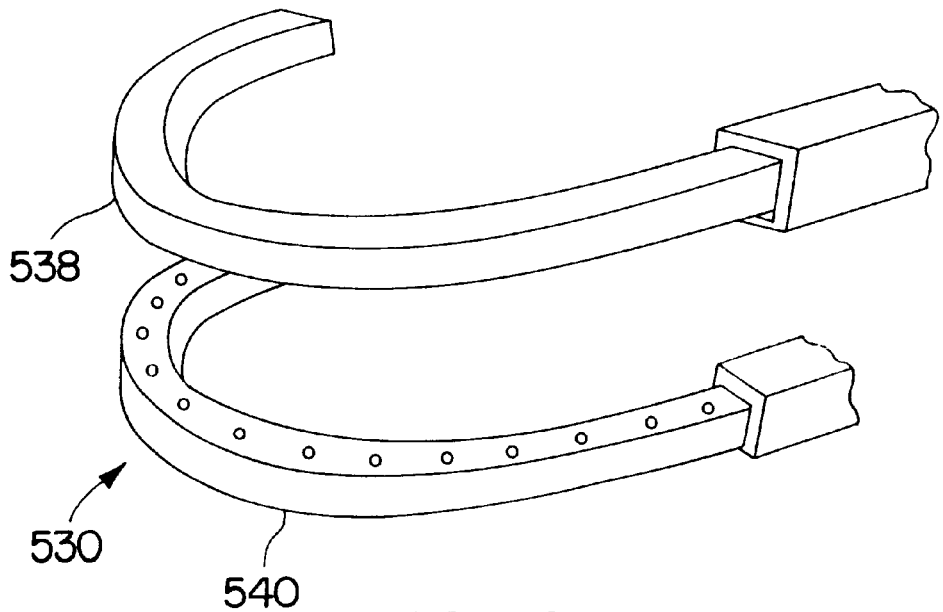
FIG. 10 is a perspective view similar to FIG. 9 of another alternative device.
Figure 11:
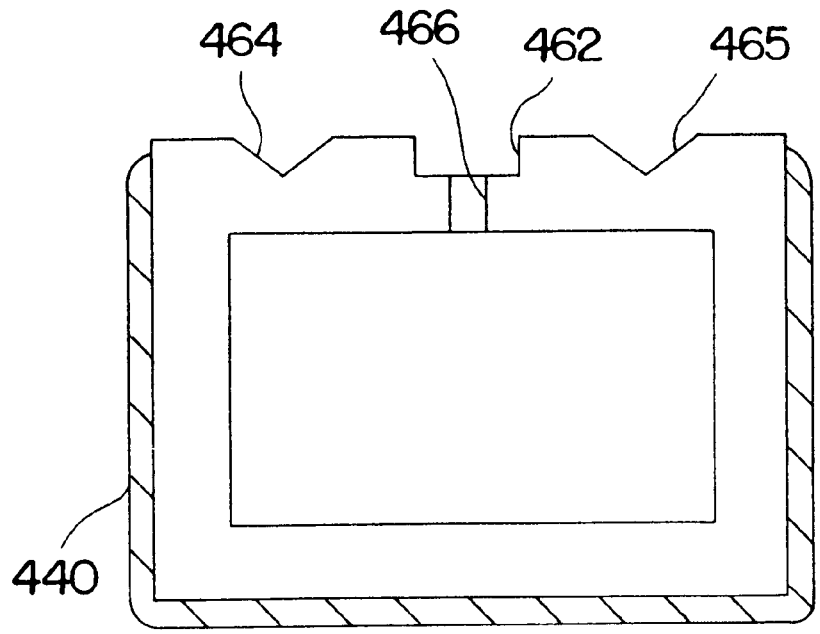
FIG. 11 is a cross-sectional view along line 11—11 of FIG. 9.

Referring to FIGS. 9 and 10, open surgical devices 430 and 530 also include jaws 438, 440 and 538, 540, respectively. The jaw portions of these devices are curved, and in the case of device 430, circular, to adapt the invention to specialized surgical situations of tissue manipulation, such as those in which fluid flow is to be terminated all around a tissue to be isolated and resected or excised. An example of such a tissue is a lesion or tumor of lung tissue. In endoscopic or open surgery, such lesions or tumors may be encircled and/or isolated, surrounding tissue sealed, and the lesions or tumors thereafter resected. Preferably, a one centimeter margin is resected about any lesion or tumor, with the lesion or tumor. As shown, the devices 430, 530 are formed of substantially square cross-section tubing, best shown in the cross-sectional drawing of FIG. 11. As most preferred, the tubing incorporates a central, depressed, cross-sectionally rectangular, and elongated groove 462 and equilaterally spaced, cross-sectionally triangular, parallel, and elongated outer grooves 464, 465. Laser drilled openings 466, similar to openings 166 described above, are located in and spaced along the central groove 462.

Figure 12:
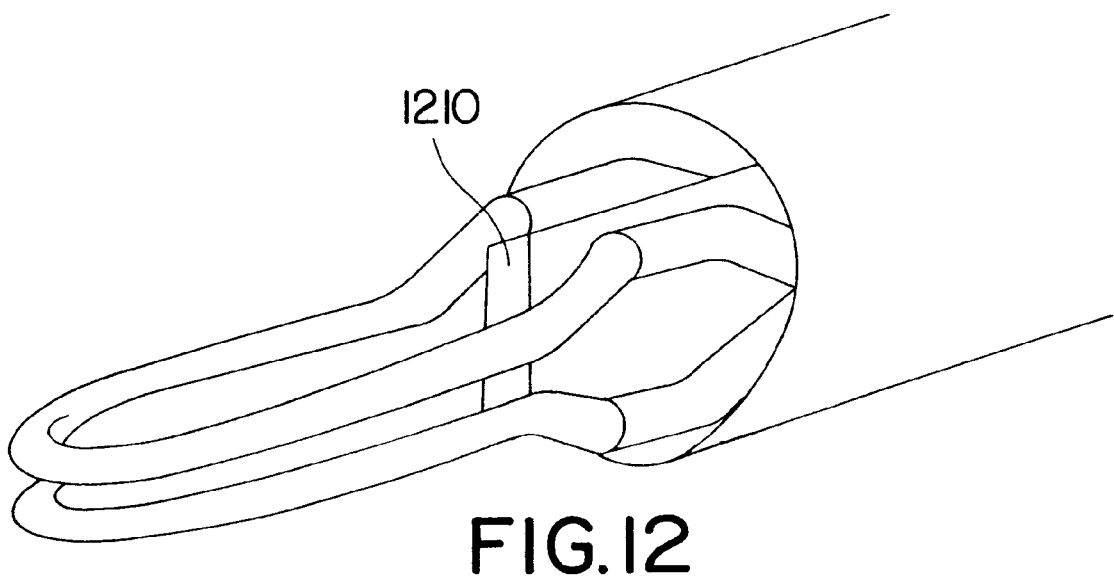
FIG. 12 is a perspective view of yet another alternative device.

Alternate cross-sectional shapes of tubing may be employed, as exemplified in FIG. 12. Flatter operative, e.g., inner faces of tubing are preferred within limits of constructing and arranging the operative faces to facilitate firm grasping and holding of tissue. Non-operative surfaces, being less of concern, may adapt to a variety of contours for a variety of alternate reasons. Further, malleable tubing may be employed, to permit the surgeon to shape the operative portions of the invented devices to specific physiological situations.

The infusion of conductive solutions, referred to here also as electrolytic solutions, simultaneously with the application of RF energy to tissues is discussed in further detail in U.S. Pat. No. 5,431,649 entitled "Method and Apparatus for R-F Ablation," in the name of Peter M. J. Mulier and Michael F. Hoey; in U.S. Pat. No. 5,609,151, entitled "Method and Apparatus for R-F Ablation," in the name of Peter M. J. Mulier. The foregoing patents are commonly assigned to the assignee of the present invention, and are incorporated by reference here.

The preferred embodiments, and the processes of making and using them, are now considered to be described in such full, clear, concise and exact terms as to enable a person of skill in the art to make and use the same. Those skilled in the art will recognize that the preferred embodiments may be altered and modified without departing from the true spirit and scope of the invention as defined in the appended claims. For example, if the invented device is incorporated in forceps, the forceps may be varied in a range from excision and cutting biopsy forceps, to endoscopic forceps, dissecting forceps, and traumatic, atraumatic and flexible endoscopic grasping forceps. The jaws may close into full and tight contact with each other, or close into spaced relationship to each other, to accommodate tissue for purposes other than cutting. As expressed above, parallel spaced relationship is considered most preferably for uniformity of application of pressure across tissue to be affected.

A variety of features such as jaw serrations, single acting and double acting jaws, closing springs, ratchet locks, fingertip rotation rings, color coding and smoke aspiration may or may not be included with the features described in detail. Devices according to the invention may be constructed and arranged to grasp, hold, fix, cut, dissect, expose, remove, extract, retrieve, and otherwise manipulate and treat organs, tissues, tissue masses, and objects. Endoscopic forceps according to the invention may be designed to be used through a trocar. Bipolar and monopolar currents may both be used. With monopolar current, grounding pads may be placed under patients. The described grooves may be eliminated in favor of alternative grooves.

For purposes of the appended claims, the term "manipulate" includes the described functions of grasping, holding, fixing, cutting, dissecting, exposing, removing, extracting, retrieving, coagulating, ablating and otherwise manipulating or similarly treating organs, tissues, tissue masses, and objects. Also for purposes of the appended claims, the term "tissue" includes organs, tissues, tissue masses, and objects. Further for purposes of the appended claims, the term "electrical energy sufficient to affect tissue" includes electrical energy sufficient to raise tissue temperature to cause non-reversible effect on tissue as described above.

To particularly point out and distinctly claim the subject matter regarded as invention, the following claims conclude this specification.

We claim:

1. An electrosurgical, tissue sealing medical device, comprising in combination:

co-operating device jaws including jaw portions for manipulating tissue;

solution infusion openings defined along the jaw portions, the solution infusion openings being constructed and arranged for receiving an electrically conductive solution and infusing the solution through the openings and along the jaw portions into tissue manipulated by the jaw portions; and an electrical conductor operatively associated with the device jaws for conducting electrical energy to the electrically conductive solution in contact with the manipulated tissue, the solution being supplied in quantity and the electrical energy being supplied in power such that energy density in the tissue in contact with the solution is in a range that seals the tissue against substantial flow of fluids;

whereby tissue many be manipulated without desiccation of the tissue at the tissue/device interface and with sealing of the tissue against substantial fluid flow from the tissue.

2. An electrosurgical, tissue sealing medical device as in claim 1, the jaw portions including opposed inner faces, the solution infusion openings being a plurality of openings defined and spaced along the inner faces.

3. An electrosurgical, tissue sealing medical device as in claim 1, further comprising:

at least one groove along at least one of said jaw portions, the solution infusion openings in the at least one jaw portion having the at least one opening located adjacent the at least one groove.

4. An electrosurgical, tissue sealing medical device as in claim 1, further comprising:

at least one groove along at least one of the jaw portions, wherein at least one of the solution infusion openings in the at least one jaw portion is located in the at least one groove.

5. An electrosurgical, tissue sealing medical device as in claim 1, further comprising a plurality of grooves along the jaw portions of the co-operating device jaws, the solution infusion openings located in the plurality of grooves.

6. An electrosurgical, tissue sealing medical device as in claim 1 further comprising:

serrations on at least one of the jaw portions.

7. An electrosurgical, tissue sealing medical device as in claim 1 further comprising:

a proximal manual handle, a shaft extending from the handle to the jaws, whereby the jaws are distally located, and a mechanism connected to the handle and jaws whereby the proximal handle manipulates the distal jaws, for endoscopic use of the device.

8. An electrosurgical, tissue sealing medical device as in claim 1 further comprising:

a pivot for pivoting movement of the jaws into contact with each other and away from contact with each other.

9. An electrosurgical, tissue sealing medical device as in claim 8 further comprising:

a blade along at least one of said jaw portions, for mechanically cutting tissue as the jaw portions are pivoted toward contact with each other.

10. An electrosurgical, tissue sealing medical device as in claim 1, further comprising:

said jaws including means for substantially uniformly compressing tissue being manipulated by the jaw portions.

11. An electrosurgical, tissue sealing medical device, comprising in combination:

co-operating device jaws including jaw portions for manipulating tissue;

solution infusion openings defined along the jaw portions, the solution infusion openings being constructed and arranged for receiving an electrically conductive solution and infusing the solution through the openings and along the jaw portions into tissue manipulated by the jaw portions; and an electrical conductor operatively associated with the device jaws for conducting electrical energy to the electrically conductive solution in contact with the manipulated tissue, the solution being supplied in quantity and the electrical energy being supplied in power such that energy density in the tissue in contact with the solution is in a range that seals the tissue against substantial flow of air;

whereby tissue many be manipulated without desiccation of the tissue and with sealing of the tissue against substantial air flow from the tissue.

12. An electrosurgical, tissue sealing medical device apparatus comprising in combination an electrosurgical, tissue sealing medical device having co-operating device jaws including jaw portions for manipulating tissue, solution infusion openings defined along the jaw portions, the solution infusion openings being constructed and arranged for receiving an electrically conductive solution and infusing the solution through the openings and along the jaw portions into tissue manipulated by the jaw portions, and an electrical conductor operatively associated with the device jaws for conducting electrical energy to the electrically conductive solution in contact with the manipulated tissue;

the apparatus further comprising a solution supply constructed and arranged to supply solution to the solution infusion openings; and an electrical supply to the solution of electrical energy;

the solution being supplied in quantity and the electrical energy being supplied in power such that energy density in the tissue in contact with the solution is in a range that seals the tissue against substantial flow of fluid.

13. An electrosurgical, tissue sealing medical device, comprising in combination:

co-operating device jaws including jaw portions for manipulating tissue, a plurality of longitudinal grooves along said jaw portions;

a pivot for pivoting movement of said jaws into contact with each other and away from contact with each other;

a plurality of solution infusion openings defined and spaced along each of the jaw portions for manipulating tissue, said solution infusion openings located in said plurality of longitudinal grooves, for receiving solution and infusing solution into the tissue along said jaw portions;

a solution supply to said plurality of solution infusion openings, for supplying solution at a rate in a range of 0.01 to 100 cc/min;

an electrical supply of electrical energy sufficient to affect tissue, to said solution supply; and an extended shaft connected to said jaws for endoscopic use of said device.

14. A medical procedure for aerostasis of a tissue, comprising:

infusing an electrolytic solution to tissue;

supplying electrical energy to said solution and thereby said tissue; and supplying the solution in quantity and the electrical energy in power sufficient to seal the tissue against air flow from the tissue.

15. A medical procedure as in claim 14, wherein the electrolytic solution is saline.

16. A medical procedure as in claim 14, wherein the solution is supplied at a rate in the range of 0.01 to 100 cc/min.

17. A medical procedure as in claim 14 wherein the electrical energy is supplied at a power in the range of 1 to 200 watts.

18. A medical procedure of manipulating thin, delicate tissue, such as connective tissue, using an enhanced solution-assisted electrosurgical medical device, an electrolytic solution source, and an electrical energy source, said device comprising in combination co-operating device jaws including jaw portions for manipulating tissue, and a plurality of solution infusion openings defined and spaced along each of the jaw portions for manipulating tissue, for receiving solution and infusing solution into the tissue along said jaw portions, the medical procedure comprising:

supplying electrolytic solution from the solution source to the solution infusion openings of said jaw portions, thereby infusing solution into tissue along the jaw portions;

supplying electrical energy from the electrical energy source sufficient to affect tissue to said solution; and manipulating tissue with said jaw portions at least in part while solution is infused into tissue along said jaw portions and electrical energy is supplied to said solution;

whereby the manipulated tissue is sealed against fluid flow from the tissue during manipulation.

19. A medical procedure of manipulating tissue as in claim 18, further comprising supplying electrical energy sufficient to affect tissue to said jaw portions.

20. A medical procedure of manipulating tissue as in claim 18, further comprising utilizing a device having jaws with jaw portions having a longitudinal dimension in a range of 0 to 6 inches, and further comprising:

supplying solution to said solution infusion openings at a rate in a range of 0.01 to 100 cc/min.

* * * * *